| United States Patent [19] | [11] Patent Number: 5,053,034 |
|---|---|
| Olerud | [45] Date of Patent: Oct. 1, 1991 |

[54] SPINAL JOINT

[76] Inventor: Sven Olerud, Malmen (Box 4), 740 11 Lännaholm, Sweden

[21] Appl. No.: 603,888

[22] Filed: Oct. 26, 1990

[30] Foreign Application Priority Data

Aug. 30, 1990 [SE] Sweden .................... 90.02569-3

[51] Int. Cl.⁵ ...................... A61F 2/44; A61F 2/30
[52] U.S. Cl. ........................ 606/61; 606/54; 606/59; 606/60; 606/72
[58] Field of Search ............... 606/60, 61, 62, 64, 606/72, 73, 59, 54; 128/69; 623/17

[56] References Cited

U.S. PATENT DOCUMENTS

| 2,391,537 | 12/1945 | Anderson | 606/54 |
|---|---|---|---|
| 2,439,995 | 4/1948 | Thrailkill | 606/72 |
| 4,483,334 | 11/1984 | Murray | 606/59 |
| 4,484,570 | 11/1984 | Sutter et al. | 606/72 |
| 4,946,458 | 8/1990 | Harms et al. | 606/61 |

FOREIGN PATENT DOCUMENTS

WO8701026 2/1987 PCT Int'l Appl. ............ 606/61

Primary Examiner—Richard J. Apley
Assistant Examiner—Karen G. Horowitz
Attorney, Agent, or Firm—Finnegan, Henderson, Farabow, Garrett & Dunner

[57] ABSTRACT

A spinal joint for use in spinal surgery includes two blocks pivotally connected to each other. One block is secured to a vertebrae with a bone screw, which the other block connects to another spinal joint. The blocks rotate relative to one another, and can be locked relative to one another in various angular positions. Serrations on one block engage with corresponding serrations in the pivotal connection portion of the second block at a selected angle, and are locked in place by a locking screw.

12 Claims, 1 Drawing Sheet

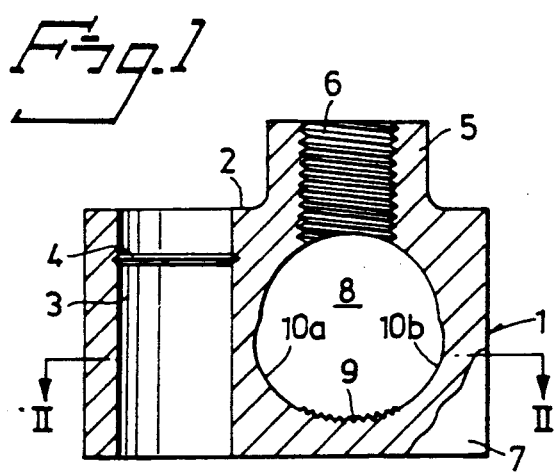
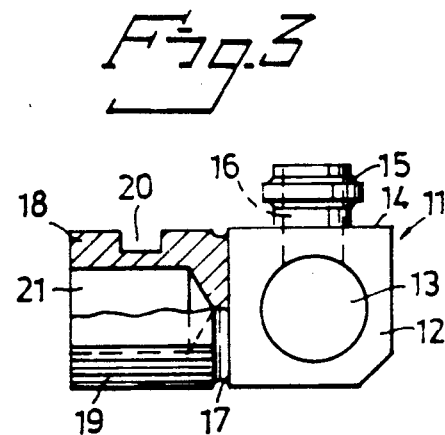
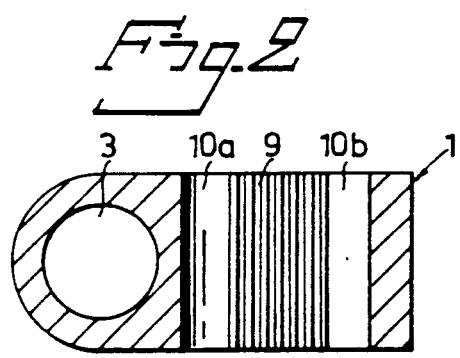
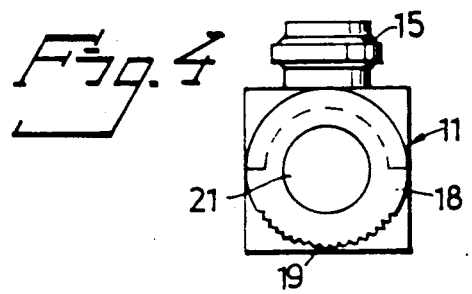
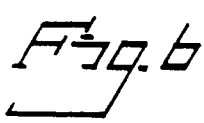
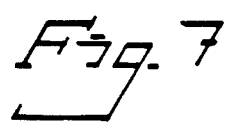
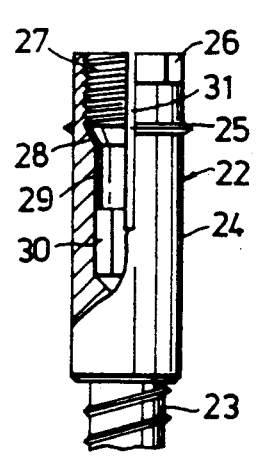
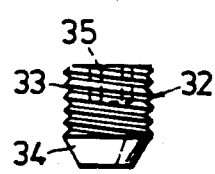
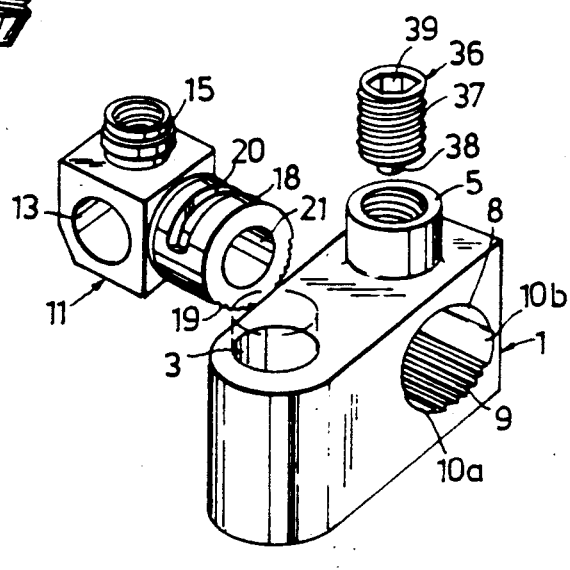

SPINAL JOINT

BACKGROUND OF THE INVENTION

1. Field of the Invention

This invention relates to a so called spinal joint.

2. Description of the Related Art

During spinal surgery in the human spine, certain fixation apparatuses are used to accomplish a displacement and subsequent fixation of vertebrae relative to each other.

The fixation apparatuses used for such and similar purposes comprise two or more body members, each of which being securable to a vertebra or bone by means of so called bone screws, and connected to each other by means of screw spindles or other rigid connection members which have the capability of changing their length. In this manner the body members may be displaced by manipulating the screw spindles or the like. The setting is secured, for instance, by blocking the rotation of the screw spindle. It will however be noted that in fixation apparatuses with more than two such body members it is usually only necessary to displace those vertebrae which are connected to the outermost body members while the vertebrae therebetween will not be displaced. In such cases, no displacement of the vertebrae connected to those body members will take place.

The body members usually are in the shape of two blocks. One block supports at least one bone screw, and the other block forms a guide for the screw spindle. These blocks are so connected to each other that they may be turned a certain angle relative to each other and then locked in the desired mutual angular position.

In the following such a body member will be called a spinal joint.

SUMMARY OF THE INVENTION

It is obvious that it is necessary to put very rigorous demands upon such spinal joints. It is thus necessary that the bone screws may be locked to the blocks, that the spinal joints may be locked relative to each other via the screw and that the blocks may be securely locked upon each angular adjustment to each other and that the lockings are so effective that the entire fixation apparatus after completed locking constitutes a single rigid and resistant unit. Especially the locking of the blocks relative to each other after an angular adjustment has proved to be difficult to carry out with sufficient effect with the minor dimensions which are requested for the apparatus. Another demand is that the surgeon will have the possibility of carrying out all adjustments or settings and lockings easily and rapidly from one single direction and the apparatus further has to be so designed that it will have as light a weight as possible. It is also important that the manufacturing costs are as low as possible.

In order to fulfill these and other objects the invention has the characteristics of the claims.

Additional objects and advantages of the invention will be set forth in the description which follows. In part, they will be obvious from the description, or may be learned by practice of the invention.

BRIEF DESCRIPTION OF THE DRAWINGS

The accompanying drawings illustrate an exemplary embodiment of the invention.

FIG. 1 shows, partly in section, the block which is intended to guide and be connected to the bone screw or bone screws, this block being called a bone screw block;

FIG. 2 is a cross-section along line II—II in FIG. 1;

FIG. 3 shows, partly in section, the block which is intended to serve as a guide for a screw spindle, this block being called a spindle block;

FIG. 4 is an end view of the spindle block;

FIG. 5 shows, partly in section, the upper portion of a bone screw;

FIG. 6 a locking member for securing the bone screw to the bone screw block; and FIG. 7 is an exploded view of the main parts of the spinal joint shown as separated from each other.

DESCRIPTION OF THE PREFERRED EMBODIMENTS

Reference will now be made in detail in the present preferred embodiment of the invention as illustrated in the accompanying drawings.

The bone screw block, generally designated by reference numeral 1, consists in the illustrated embodiment of a body which has the substantial shape of a square or rectangular body. From the upper surface 2 of block 1 extends a through, in the drawing vertical, hole 3. At a distance from the upper surface 2, hole 3 has a circumferential groove 4 for a purpose to be described. Upper surface 2 also has an upstanding portion 5 which has a threaded hole 6, which opens into an opening 8 extending from the front surface 7 of the body. This opening 8 has in the portion thereof which is remote from the threaded hole 6 a serrated portion 9, which in a preferred embodiment extends over an angular distance of about 60°. At each side of said serrated portion there are grooved portions 10a, 10b for a reason to be explained.

The spindle block, generally designated as 11, also consists of a body having a front surface 12. A through hole 13 extends from front surface 12. From the upper surface 14 of spindle block 11 extends an upstanding portion 15, which has a threaded hole 16 which opens into the hole 13 perpendicular thereto. From one side 17 of the body further extends a substantially cylindrical stud 18, which in the lower portion, referring to FIGS. 3 and 4, has a serrated portion 19, which in a preferred embodiment extends over an angular space of about 120°. In the upper portion thereof, the stud 18 further has a circumferential preferably milled groove 20, which according to FIG. 4 suitably extends over an angular distance of about 180° and which preferably has a constant depth. In the stud 18 there is provided an axial hole 21.

In the illustrated preferred embodiment the bone screws are designed as shown in FIG. 5. Said bone screws 22 each have substantially plain and cylindrical upper portion 24, and a threaded lower portion 23 of a conventional design. The upper portion 24 however has at a distance from the upper edge thereof a circumferential ridge 25, which preferably has the same profile as the groove 4 in the bone screw block, for instance triangular in section, and which is provided to fit into the groove 4. The upper portion of the bone screw further has an exterior key 26, for instance a hexagonal portion, and from the upper end surface there extends a central, axial, threaded hole 27, which continues in a tapered portion 28, which in turn continues in a lower hole 29, which preferably ends in or forms an interior key, for instance a hexagonal portion, 30.

By means of two or more axial slots 31 the upper part of the bone screw is divided into a number of resilient segments. This makes it possible to press a bone screw block 1 onto a bone screw 22, screwed into a vertebra whereupon the ridge 25 will snap into the groove 4 when it has been brought into register therewith. It is obvious that the bone screw then can be locked to the bone screw block against axial movements as well as against turning by using a locking element of the kind shown in FIG. 6 and denoted 32. This locking element 32 has an exterior thread 33 which corresponds to the interior thread 27 in the upper part of the bone screw. Locking element 32 also has an exterior tapered portion 34 which is so dimensioned that, by cooperation with the internal tapered portion 28 of the bone screw, it will bring forth an expansion of the upper part of the bone screw. When the locking element is screwed in by means of a key which fits into an internal key 35 the expansion takes place and as a consequence thereof a very effective locking of the bone screw or the bone screws in relation to the bone screw block or blocks is effected.

From the exploded view in FIG. 7 the shape and cooperation of the various parts may be appreciated. To establish the pivotal connection between the spindle block 11 and the bone screw block 1, the stud 18 of the former is introduced into the hole 8 of the latter. Between the stud 18 and the hole 8 there exists a play which somewhat exceeds the depth of the serrations 9 and 19 respectively. In a preferred embodiment said serrations which preferably may have a trapezoid profile have a depth of about 0.2 mm but the pitch of the serrations 19 of the stud 18 is somewhat bigger than the corresponding pitch of the serrations 9 of the hole 8. In the preferred dimensions, where the stud has a diameter of about 8 mm and the serrations are about 0.2 mm deep the stud preferably has 69 serrations/turn, i.e. for the area 120°=23 serrations while the hole 8 has 72 serrations/turn, i.e. for the angular area 60°=12 serrations. Owing to the play between the stud 18 and the hole 8, the spindle block 11 and the bone screw block 1 may be pivoted relative to each other. It is obvious that such pivoting may be prevented by bringing serrations 19 into engagement with serrations 9. This is accomplished by means of a locking screw 36 (see FIG. 7) which has an exterior thread 37 which cooperates with the internal thread of the bone screw block 1 and a turned down end portion 38, which fits into the groove 20 of the stud 18 of the spindle block 11.

After setting the blocks 1 and 11, which in the illustrated embodiment may be pivoted 60° relative to each other, the set position is locked by screwing in the screw 36, which for that purpose has an interior key 39, such that the end surface of the end portion 38 thereof will be pressed against the bottom of the groove 20. This brings forth a radial displacement of the stud. The serrations are then guided into each other and an extremely effective locking is obtained since the serrations in this position exactly fit into each other. The serrations 19 which are not engaging the serrations 9 will then be out of contact with the wall portions surrounding the hole thanks to the recesses 10a, 10b. Since the end portion 38 of the locking screw 36 engages the groove 20, the blocks may be pivoted relative to each other as long as said end portion 38 is received in the groove 20 but has not been pressed against the bottom thereof. The pivoting may be carried out without risk of tilting and at the same time the force which brings the serrations 9 and 19 into engagement with each other will always act in a radial direction towards the serrations 9.

The spinal joint now described may of course be varied in many respects within the scope of the claims. The serrations may of course be substituted by ridges which engage in the spaces between other such ridges. Special steps may be taken to further lock settings, respectively facilitating the operation. Thus, the upstanding portion 5 may have a deformable upper portion which by deformation may prevent the unintentional unscrewing of the locking screw. In order to facilitate the adjustment of the blocks 1 and 11 in relation to each other, so called reposition means may be used. Such a means may for instance be detachably connected to the stud 18 by having a part which is insertable in the hole 21 of said stud.

The parts of the spinal joint are preferably made of steel but other suitable materials may of course be chosen and the design of the members may also be varied according to actual needs.

The term block is to be understood only as a body the shape of which therefore may be rounded, faceted or the like. The term serration means a toothing, where peripherally spaced grooves or ridges may engage each other to prevent a relative movement perpendicular to the lengthwise direction of said grooves or ridges.

It should further be mentioned that the clearance between the stud and the hole need not be apparent in all radial directions and that the profile of the toothing may be triangular or have any suitable shape.

Additional modifications will readily occur to those skilled in the art. The invention, in its broader aspects, is not limited to the specific details shown and described. Departures may be made from such details without departing from the scope of the invention, which is established by the claims and their equivalents.

I claim:
1. A spinal joint, comprising:
   a first block portion for connection to a human spine, including opposite face surface portions and a side surface portion connecting said face surface portions, said first block portion defining a first aperture extending between said opposite face surface portions, and a second aperture extending from said side surface portion to said first aperture, said first aperture having a peripheral surface, a portion of said peripheral surface being grooved by a first plurality of serrations;
   a second block portion for connection to an adjacent spinal joint, including a projecting portion extending into said first aperture of said first block portion, said projecting portion having a peripheral surface grooved by a second plurality of serrations, said first and second block portions rotatable relative to one another; and
   locking means for locking said first and second block portions in a selected one of a plurality of angular positions relative to one another, said locking means including a removable pin portion extendable into said second aperture of said first block portion for contacting said peripheral surface of said projecting portion of said second block portion and displacing said projected portion of said second block portion to engage at least one of the first plurality of serrations with at least one of the second plurality of serrations.

2. A spinal joint according to claim 1, wherein said second plurality of serrations in the peripheral surface of said projecting portion extend around less than 180° of a circumference of said peripheral surface.

3. A spinal joint according to claim 1, wherein said second plurality of serrations in the peripheral surface of said projecting portion extend around approximately 120° of a circumference of said peripheral surface.

4. A spinal joint according to claim 1, wherein said first plurality of serrations in the peripheral surface of said first aperture extend around a first portion of a circumference of said peripheral surface of said first aperture, and said second plurality serrations in the peripheral surface of said projecting portion extend around a second portion of a circumference of said peripheral surface of said projecting portion, said first portion being approximately one half of said second portion.

5. A spinal joint according to claim 4, wherein said peripheral surface of said first aperture includes grooved recesses on at least one side of said first plurality of serrations.

6. A spinal joint according to claim 5, wherein at least one of said second plurality of serrations extends into one of said grooved recesses at times when said first and second block portions are locked in one of the plurality of angular positions relative to one another.

7. A spinal joint according to claim 1, wherein the peripheral surface of said projecting portion further includes a groove portion, and said removable pin portion of said locking means is configured to extend into said groove portion of said projecting portion.

8. A spinal joint according to claim 1, wherein said first plurality of serrations have a first pitch, and the second plurality of serrations have a second pitch, said second pitch being greater than said first pitch.

9. A spinal joint according to claim 8, wherein said first pitch is approximately 72 serrations in a 360° circumference, and said second pitch is approximately 69 serrations in a 360° circumference.

10. A spinal joint according to claim 1, further including a third aperture defined by said first block portion, and bone screw means extendable through said third aperture for connecting said first block portion to the human spine.

11. A spinal joint according to claim 10, wherein said third aperture has an inner peripheral surface including a depression portion encircling said third aperture peripheral surface, and said bone screw means includes a bone screw having a peripheral surface including a ridge portion encircling said bone screw peripheral surface, said ridge portion of said bone screw being engageable with said depression portion of said third aperture.

12. A spinal joint according to claim 10, wherein said bone screw means includes a bone screw having a plurality of slots defining a plurality of resilient segments, and a bone screw locking means insertable into said bone screw for expanding said resilient segments in a radial direction to engage a peripheral surface of said third aperture.

* * * * *